United States Patent [19]

Sugg

[11] Patent Number: 5,780,464
[45] Date of Patent: *Jul. 14, 1998

[54] ENTERIC COATED COMPOSITIONS OF 1,5-BENZODIAZEPINE DERIVATIVES HAVING CCK ANTAGONISTIC OR AGONISTIC ACTIVITY

[75] Inventor: Elizabeth Ellen Sugg, Durham, N.C.

[73] Assignee: Glaxo Wellcome Inc., Research Triangle Park, N.C.

[*] Notice: The term of this patent shall not extend beyond the expiration date of Pat. No. 5,646,140.

[21] Appl. No.: 817,364

[22] PCT Filed: Oct. 13, 1995

[86] PCT No.: PCT/US95/12829

§ 371 Date: Apr. 14, 1997

§ 102(e) Date: Apr. 14, 1997

[87] PCT Pub. No.: WO96/11701

PCT Pub. Date: Apr. 25, 1996

[30] Foreign Application Priority Data

Oct. 14, 1994 [GB] United Kingdom ............... 9420748

[51] Int. Cl.$^6$ ........................................ A61K 31/55
[52] U.S. Cl. ................................................. 514/221
[58] Field of Search .................................... 514/221

[56] References Cited

U.S. PATENT DOCUMENTS 5,646,140   7/1997   Sugg et al.

FOREIGN PATENT DOCUMENTS

A 90 06937   6/1990   WIPO.
A 93 14074   7/1993   WIPO.
A 94 24149   10/1994  WIPO.

Primary Examiner—William R. A. Jarvis
Attorney, Agent, or Firm—Robert H. Brink

[57] ABSTRACT

A pharmaceutical formulation in solid dosage form for oral administration which comprises a compound of the general Formula (I)

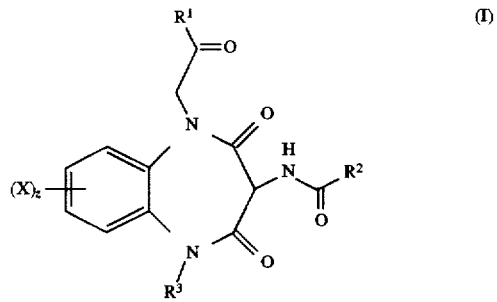

or a physiologically acceptable salt or solvate thereof together with one or more pharmaceutically acceptable carriers wherein the formulation is encased in an enteric coating or capsule.

10 Claims, No Drawings

ENTERIC COATED COMPOSITIONS OF 1,5-BENZODIAZEPINE DERIVATIVES HAVING CCK ANTAGONISTIC OR AGONISTIC ACTIVITY

This application is filed pursuant to 35 U.S.C. § 371 as a United States National Phase Application of International Application No. PCT/US95/12829, filed 13 Oct. 1995 which claims priority from GB 9420748.7, filed 14 Oct. 1994.

This invention relates to pharmaceutical compositions containing novel 1,5-benzodiazepine derivatives which exhibit agonist activity for CCK-A receptors thereby enabling them to modulate the hormones gastrin and cholecystokinin (CCK) in mammals.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxyl terminal octapeptide, CCK-8 (also a naturally occurring neuropeptide), and 39- and 12-amino acid forms. Gastrin occurs in 34-, 17- and 14-amino acid forms, with the minimum active sequence being the C-terminal tetrapeptide, Trp-Met-Asp-Phe-$NH_2$ (CCK4) which is the common structural element shared by both CCK and gastrin.

CCK and gastrin are gastrointestinal hormones and neurotransmitters in the neural and peripheral systems and perform their respective biological roles by binding to particular receptors located at various sites throughout the body. There are at least two subtypes of cholecystokinin receptors termed CCK-A and CCK-B and both are found in the periphery and in the central nervous system.

The CCK-A receptor, commonly referred to as the "peripheral-type" receptor, is primarily found in the pancreas, gallbladder, ileum, pyloric sphincter and on vagal afferent nerve fibers. Type-A CCK receptors are also found in the brain in discrete regions and serve to provide a number of CNS effects. Due to the ability of CCK-8 and Type-A CCK-selective agonists to suppress food intake in several animal species, considerable interest has been generated toward the development of new substances which function as Type-A receptor-selective CCK agonists in order to serve as anorectic agents.

The CCK-B or gastrin receptors are found in peripheral neurons, gastrointestinal smooth muscle and gastrointestinal mucosa, most notably in parietal cells, ECL cells, D cells and chief cells. CCK-B receptors also predominate in the brain and have been implicated in the regulation of anxiety, arousal and the action of neuroleptic agents.

U.S. Pat. No. 4,988,692, to Gasc, et al. describes a group of 3-acylamino 1-alkyl-5-phenyl 1,5-benzodiazepine derivatives which behave as cholecystokinin antagonists to reverse or block the effects of the endogenous hormone at its receptors.

U.S. Pat. No. 4,490,304 and PTC applications No's W090/06937 and W091/19733 describe peptide derivatives that exhibit CCK-A agonist activity. Such compounds have been disclosed for appetite regulation as well as the treatment and/or prevention of gastrointestinal disorders or disorders of the central nervous in animals and, more particularly, humans.

We have now discovered that the bioavailability following oral administration of a novel group of 3-amino 1,5-benzodiazepine compounds which exhibit a agonist activity for the CCK-A receptor may be significantly increased if the compound is administered in a solid dosage form the outer layer of which is an enteric coating or shell.

The present invention thus provides a pharmaceutical formulation in solid dosage form for oral administration which comprises a compound of the general Formula (I)

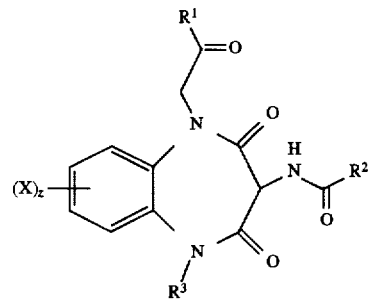

and physiologically salts and solvate thereof wherein:
X is either hydrogen, trifluoromethyl, alkyl, $C_{1-4}$alkylthio, —O($C_{1-4}$alkyl) or halogen;
$R^1$ is either Formula II or —$NR^4R^5$;

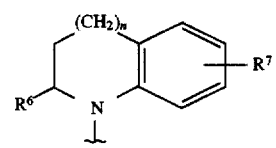

$R^2$ is either:
(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxobenzopyran may optionally be substituted in the benzo ring thereof by the group $R^9$ as defined hereunder or
(2) phenyl or phenyl mono- or disubstituted independently with halogen, hydroxy, cyano, carboxy, —O($C_{1-4}$alkyl), —O($CH_2C_6H_5$), —COO($C_{1-4}$alkyl), amino, dimethylamino, —$NHR^{10}$, 1-pyrrolidinyl or tetrazolyl; or
(3) pyridine or pyridinyl mono- or disubstituted independently with halogen, methyl, hydroxy, nitro, cyano, carboxy, —O($C_{1-4}$ alkyl), —O($CH_2C_6H_5$), —COO($C_{1-4}$alkyl), amino or dimethylamino; or
(4) —$NHR^{11}$ where $R^{11}$ is defined hereinunder or $R^{11}$ is 7-indazolyl containing a group $R^{10}$ at the N-1 position;

$R^3$ is hydrogen, $C_{1-6}$alkyl, $C_{3-6}$cycloalkyl, phenyl or phenyl mono- or disubstituted independently with halogen;

$R^4$ is independently $C_{3-6}$alkyl, $C_{3-6}$cycloalkyl, $C_{3-6}$alkenyl, phenyl, —$(CH_2)_pCN$ or —$(CH_2)_pCOO(C_{1-4}$alkyl) and $R^5$ is independently $C_{3-6}$alkyl, $C_{3-6}$cycloalkyl, $C_{3-6}$ alkenyl, benzyl, phenyl or phenyl mono- or disubstituted independently with $C_{1-3}$alkyl optionally substituted with 1 or more fluorine atoms, cyano, hydroxy, dimethylamino, —O($C_{1-4}$alkyl), —O($CH_2C_6H_5$), —NH($C_{1-4}$alkyl), —COO($C_{1-4}$alkyl), —N($C_{1-4}$alkyl)$_2$ pyrrolidino, morpholino or halogen or $R^4$ is $C_{1-2}$alkyl and $R^5$ is phenyl substituted at the 2- or 4-position with chloro, methyl, methoxy or methoxycarbonyl;

$R^6$ is hydrogen or methyl;

$R^7$ is hydrogen, hydroxy, fluoro, dimethylamino, —O($C_{1-4}$alkyl) or —O($CH_2C_6H_5$);

$R^8$ is —$(CH_2)_bCOOH$;

$R^9$ is methyl, chloro, nitro, hydroxy, methoxy or —$NHR^{10}$;

$R^{10}$ is hydrogen, acetyl, $C_{1-4}$alkyl, —S)$_3$H, —SO$_2$CH$_3$, —SO$_2$CF$_3$ or —SO$_2$C$_6$H$_5$, $C_{1-4}$alkoxycarbonyl;

$R^{11}$ is phenyl or phenyl mono- or disubstituted independently with fluorine, trifluoromethoxy, $C_{1-4}$alkylthio, —(CH$_2$)$_c$COOH, —(CH$_2$)$_c$COO(C$_{1-4}$alkyl), —(CH$_2$)$_c$SCH$_3$, —(CH$_2$)$_c$SOCH$_3$, —(CH$_2$)$_c$SO$_2$CH$_3$, —(CH$_2$)$_c$CONH$_2$, —SCH$_2$COOH, —CONH(SO$_2$CH$_3$), —CONH(SO$_2$CF$_3$), —(CH$_2$)$_c$N(C$_{1-4}$alkyl)$_2$, —(CH$_2$)$_c$NH(SO$_2$CF$_3$), —(CH$_2$)$_c$N(SO$_2$CF$_3$)(C$_{1-4}$alkyl), —(CH$_2$)$_c$SO$_2$NHCO(C$_{1-4}$alkyl), —(CH$_2$)$_c$SO$_2$N(C$_{1-4}$alkyl)CO(C$_{1-4}$alkyl), —(CH$_2$)$_c$CONHSO$_2$(C$_{1-4}$alkyl), —(CH$_2$)$_c$CON(C$_{1-4}$alkyl)SO$_2$(C$_{1-4}$alkyl), —(CH$_2$)$_c$OR$^{12}$ —(CH$_2$)$_c$NHR$^{10}$ or phenyl monosubstituted with —(CH$_2$)$_c$(tetrazolyl), —(CH$_2$)$_c$(carboxamidotetrazolyl) or —(CH$_2$)$_c$(pyrrolidinyl) or R$^{11}$ is selected from pyridine or pyridinyl mono- or disubstituted independently with halogen, methyl, hydroxy, nitro, cyano, carboxy, —O(C$_{1-4}$ alkyl), amino, dimethylamino, —NHR$^{10}$;

$R^{12}$ is hydrogen, $C_{1-6}$alkyl, $C_{3-6}$cycloalkyl, —CH$_2$C$_6$H$_5$, —CH$_2$COOH, —CH$_2$CONH$_2$, —CH$_2$CONH(C$_{1-4}$alkyl), —CH$_2$CON(C$_{1-4}$alkyl)$_2$ or

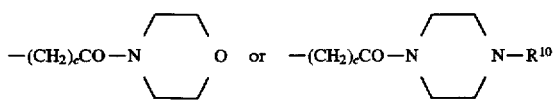

z is 1 or 2;
n is 1 or 2;
p is an integer from 1–4;
b is an integer from 0–3; and
c is 0 or 1.

together with one or more pharmaceutically acceptable carriers, wherein the formulation is encased in an enteric coating or capsule.

Conveniently the formulation according to the invention is in the form of a tablet coated with a conventional enteric coating. Alternatively the formulation according to the invention may be presented in the form of a capsule the shell of which is made from enteric material or is coated with an enteric material.

In the context of this application it will be understood that the term enteric coating or material refers to a coating or material that will pass through the stomach essentially intact but will rapidly disintegrate in the small intestine to release the active drug substance.

The tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc polyethylene glycol or silica), disintegrants (for example, potato starch or sodium starch glycollate) or wetting agents, such as sodium lauryl sulphate. The enteric coatings may be applied to the tablets and/or capsules according to methods well-known in the art.

Suitable enteric coatings for use in the invention will be these coatings known to those skilled in the art. Such coatings include cellulose acetate phthalate, polyvinyl acetate phthalate, shellac, styrene maleic acid copolymers, methyacrylic acid copolymers and hydroxypropyl methyl cellulose phthalate. The said coatings may also contain a plasticizer and or a dye.

In the compounds of formula (I) when $R^1$ represents the group of Formula (II), examples of such a group include those wherein $R^6$ is hydrogen or more examples of such a group include those wherein $R^6$ is hydrogen or more particularly methyl, $R^7$ is hydrogen, hydroxyl, methoxy, or fluorine, and n is 1.

When $R^1$ represents the group NR$^4$R$^5$, examples of suitable groups include those wherein $R^4$ represent $C_{3-6}$ alkyl, such as propyl or isopropyl, cyclohexyl or phenyl and $R^5$ represents $C_{3-6}$ alkyl, benzyl or phenyl optionally substituted in the para- position by hydroxy, dimethylamino methoxy, trifluoromethyl, fluorine, pyrrolidino or morpholino. Within this group, particularly useful $R^1$ groups include those wherein $R^4$ is propyl and, more particularly, isopropyl and $R^5$ represents phenyl or phenyl substituted in the para-position by groups selected from hydroxy, methoxy dimethylamino, fluorine, or morpholino.

Examples of particularly suitable $R^1$ groups include those wherein $R^1$ is the group of Formula (II) wherein $R_6$ is methyl, n is 1 and $R^7$ is hydrogen, hydroxy, fluorine or methoxy or $R^1$ is the group NR$^4$R$^5$ wherein $R^4$ is propyl or isopropyl and $R^5$ is phenyl optionally substituted in the para position by a group selected from hydroxy, methoxy, fluoro, dimethylamino, pyrrolidino or morpholino.

When $R^2$ represents a group selected from indole, indoline, benzofuran, benzothiophene, quinoline or 4-oxobenzopyran, the optional substituent $R^9$ is conveniently a group selected from hydrogen, methyl, methoxy, hydroxy, nitro or amino and, where appropriate, the optional substituent on nitrogen, (R$^8$), is —CH$_2$CO$_2$H.

When $R^2$ is an optionally substituted phenyl group, this is conveniently phenyl or phenyl substituted by one or two groups, which may be the same or different and selected from chlorine, fluorine, amino, hydroxy or carboxyl.

When $R^2$ represents the group NHR$^{11}$, $R^{11}$ is conveniently phenyl (optionally substituted by fluoro, hydroxy, amino, dimethylamino, trifluoromethylsulphonylamino, $C_{1-4}$ alkoxycarbonyl, carboxy, 1H-tetrazol-5-yl, acetylamino or OR$^{12}$ wherein $R^{12}$ represents hydrogen, methyl, benzyl, CH$_2$CO$_2$H, CH$_2$CONH$_2$, CH$_2$CONHCH$_3$, CH$_2$CON(CH$_3$)$_2$

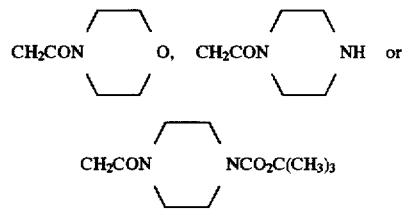

or a 7-indazolyl group wherein the N-1 substituent, (R$^{10}$), is hydrogen.

When $R^{11}$ is a mono substituted phenyl group, the substituted is conveniently in the meta- position.

Examples of particularly suitable $R^2$ groups includes indole, benzofuran, thiophene, benzothiophene, indoline, quinoline, 4-oxobenzopyran, an optionally substituted phenyl group or the group NHR$^{11}$. Conveniently, $R^2$ is selected from the group indole, indoline or benzofuran, an optionally substituted phenyl group or the group NHR$^{11}$. More particularly, $R^2$ represents an indole, an optionally substituted phenyl or NHR$^{11}$.

When $R^3$ represents $C_{1-6}$ alkyl, examples of suitable groups include methyl, ethyl, propyl, isopropyl, butyl, t-butyl or isoamyl.

When $R^3$ represents $C_{3-6}$ cycloalkyl, examples of suitable groups include cyclopropyl, cyclopentyl or cyclohexyl.

When $R^3$ represents phenyl, mono or disubstituted by independently with halogen, examples of suitable groups include those wherein the halogen substituent is fluorine e.g., 2-fluorophenyl or 4 fluorophenyl.

Examples of particularly suitable $R^3$ groups include hydrogen, methyl, cyclohexyl, 2-fluorophenyl or phenyl, and more particularly, phenyl.

A particularly useful group of compounds for use in the formulations according to the invention include those wherein $R^1$ represents the group of Formula (II) wherein $R^6$ is methyl, n is 1 and $R^7$ is hydrogen, fluorine, hydroxy or methoxy, or more particularly $NR^4R^5$ wherein $R^4$ is propyl or isopropyl and $R^5$ is phenyl optionally substituted in the para position by a group selected from hydroxy, methoxy, fluoro, dimethylamino or monopholino; $R^2$ represents phenyl (optionally substituted independently by one or two groups selected from chlorine, fluorine, hydroxy, amine or carboxy), $NHR^{11}$ wherein $R^{11}$ represents phenyl (optionally substituted by amino, dimethylamino, trifluoromethylsulphonylamino, carboxy, 1H-tetrazol-5-yl, acetylamino or $OR^{12}$ wherein $R^{12}$ represents hydrogen, methyl, benzyl, $CH_2CO_2H$, $CH_2CONH_2$, $CH_2CONHCH_3$, $CH_2CON(CH_3)_2$,

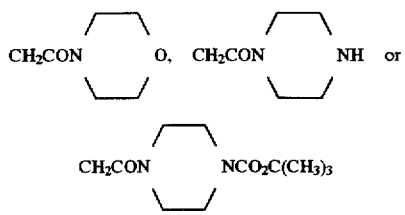

wherein the substituent is preferably in the meta- position) or an indole wherein the nitrogen atom is optionally subtituted by the group —$CH_2CO_2H$ and the benzo ring is optionally substituted by chlorine, methyl, methoxy, nitro, hydroxy or amino; $R^3$ represents hydrogen, methyl, cyclohexyl, 2-fluorophenyl or phenyl or, more particularly, 2 fluorophenyl or phenyl; and X represents fluorine and z is 1 or, more particularly, X is hydrogen;

A particularly interesting class of compounds for use in the formulation according to the present invention because they exhibit a very high and selective affinity for the CCK-A receptor as well as exceptional efficacy are those wherein $R^2$ is an indole group. A preferred group of compounds within this class are those wherein the indole group is substituted on the nitrogen atom by the group —$CH_2CO_2H$ or, more preferably, the nitrogen atom is unsubstituted, and benzo ring of the indole group is optionally substituted by a group selected from chlorine, methyl, methoxy, nitro, hydroxy or amino.

A particularly preferred compound for use in the formulation according to the invention is:

1 H-Indole-2-carboxylic acid {1-[Isopropyl-(4-methoxyphenyl)carbamoyl-methyl]-2,4-dioxo-5-phenyl-2,3,4,5-tetrahydro-1H-benzo[b][1,4]diazepin-3-yl}-amide and enantiomers thereof.

As provided herein, the term alkyl is generally intended to mean both straight chain and branched chain aliphatic isomers of the corresponding alkyl. For example, $C_{1-6}$alkyl is intended to include methyl, ethyl, n-propyl, isopropyl, n-butyl, isobutyl, tertbutyl, n-pentyl, etc.

The term cycloalkyl, as provided herein, is intended to mean all alicyclic isomers of the corresponding alkyl. For example, the term $C_{3-6}$ alkyl, as provided herein, is intended to include such groups as cyclopropyl, cyclopentyl and cyclohexyl.

The term halogen is intended to mean F, Cl, Br or I.

The term tetrazole as a group or part of a group refers to the (1 H)-tetrazol-5-yl grouping and tautomers thereof.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of Formula (I) include conventional salts formed from pharmaceutically acceptable inorganic or organic acids as well as quaternary ammonium acid addition salts. More specific examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts. References hereinafter to a compound for use in the invention include both compounds of Formula (I) and their pharmaceutically acceptable salts and solvates.

The compounds of formula (I) exhibit CCK-A agonist activity and can be considered full or partial cholecystokinin agonists in that they bind to CCK-A receptors and either fully or partially stimulate gallbladder contraction and/or reduce feeding in animal paradigms.

As agonists of CCK-A receptors, the compounds of formula (I) are useful anorectic agents advantageous in the treatment of obesity as well as related pathologies, such as diabetes or hypertension. Moreover, the compounds disclosed herein provide for new approaches for inducing satiety, providing for appetite regulation and modifying food intake in mammals, especially humans, to regulate appetite, treat obesity and maintain weight loss.

Additionally, certain compounds of formula (I) may also exhibit some antagonist activity at particular site-specific CCK-B and gastrin receptors as demonstrated by their inhibition of CCK-4 stimulated contraction of isolated guinea-pig ileum longitudinal muscle-myenteric plexus and pentagastrin-stimulated acid secretion in rat isolated gastric mucosa using the procedures described by M. Patel and C. F. Spraggs in Br. J. Pharmac., (1992), 106, 275–282 and by J. J. Reeves and R. Stables in Br. J. Pharmac., (1985), 86, 677–684.

The relative affinities of compounds of formula (I) for the CCK-A and CCK-B receptors may be determined using known conventional procedures such as described by Fornos et al J. Pharmacol Exp. Ther., 1992 261,1056–1063.

The ability of compouds of formula (I) to inhibit gastric acid secretion, such as pentagastrin stimulated acid secretion may be determined in the conscrious gastric fistula rat using methods described by Hedges and Parsons Journal of Physiology 1977, 267 191–194.

According to a further aspect of the present invention, there is provided herein a method for the treatment of a mammal, including man, in particular in the treatment conditions where modification of the effects of CCK and/or gastrin is of therapeutic benefit, the method comprising administering to the patient an enterically coated tablet or capsule containing a therapeutically effective amount of a compound of Formula (I) or a pharmaceutically acceptable salt or solvate thereof.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1-1500 mg per day. The desired dose may conveniently be presented in a single dose or as divided doses administered at appropriate intervals, for example as two, three, four or more sub-doses per day.

Compounds of general Formula (I), methods for their preparation and their activity as CCK-A agonists are described in WO9424149.

EXAMPLE

The following example illustrates the invention but should not be construed as a limitation thereto.

Tablet

| | |
|---|---|
| Active Ingredient | 50 mg |
| Lactose anhydrous USP | 163 mg |
| Microcrystalline Cellulose NF | 69 mg |
| Pregelatinized starch Ph. Eur. | 15 mg |
| Magnesium stearate USP | 3 mg |
| Compression weight | 300 mg |

The active ingredient, microcrystalline cellulose, lactose and pregletinized starch are sieved through a 500 micron sieve and blended in a suitable mixer. The magnesium starate is sieved through a 250 micron sieve and blended with the active blend. The blend is compressed into tablets using suitable punches, then coated with cellulose acetate phthalate in a conventional manner.

I claim:

1. A pharmaceutical formulation in solid dosage form for oral administration which comprises a compound of Formula (1)

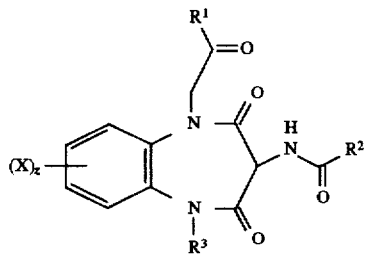

or physiologically acceptable salts or solvates thereof wherein:

X is either hydrogen, trifluoromethyl, alkyl, $C_{1-4}$alkylthio, —O($C_{1-4}$alkyl) or halogen;

$R^1$ is either Formula II or —$NR^4R^5$;

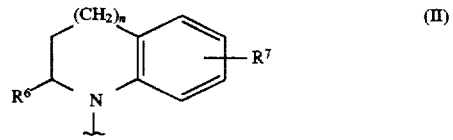

$R^2$ is either:

(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxobenzopyran may optionally be substituted in the benzo ring thereof by the group $R^9$ as defined hereunder or (2) phenyl or phenyl mono- or disubstituted independently with halogen, hydroxy, cyano, carboxy, —O($C_{1-4}$alkyl), —O($CH_2C_6H_5$), —COO($C_{1-4}$a-alkyl), amino, dimethylamino, —$NHR^{10}$, 1-pyrrolidinyl or tetrazolyl; or (3) pyridine or pyridinyl mono- or disubstituted independently with halogen, methyl, hydroxy, nitro, cyano, carboxy, —O($C_{1-4}$ alkyl), —O($CH_2C_6H_5$), —COO($C_{1-4}$alkyl), amino or dimethylamino; or (4) —$NHR^{11}$ where $R^{11}$ is defined hereinunder or $R^{11}$ is 7-indazolyl containing a group $R^{10}$ at the N-1 position;

$R^3$ is hydrogen, $C_{1-6}$alkyl, $C_{3-6}$cycloalkyl, phenyl or phenyl mono- or disubstituted independently with halogen;

$R^4$ is independently $C_{3-6}$alkyl, $C_{3-6}$cycloalkyl, $C_{3-6}$alkenyl, phenyl, —$(CH_2)_pCN$ or —$(CH_2)_pCOO$ ($C_{1-4}$alkyl) and $R^5$ is independently $C_{3-6}$alkyl, $C_{3-6}$cycloalkyl, $C_{3-6}$alkenyl, benzyl, phenyl or phenyl mono- or disubstituted independently with $C_{1-3}$alkyl, cyano, hydroxy, dimethylamino, —O($C_{1-4}$alkyl), —O($CH_2C_6H_5$), —NH($C_{1-4}$alkyl), —COO($C_{1-4}$alkyl), —N($C_{1-4}$alkyl)$_2$ pyrrolidino, morpholino or halogen or $R^4$ is $C_{1-2}$alkyl and $R^5$ is phenyl substituted at the 2- or 4- position with chloro, methyl, methoxy or methoxycarbonyl;

$R^6$ is hydrogen or methyl;

$R^7$ is hydrogen, hydroxy, fluoro, dimethylamino, —O($C_{1-4}$alkyl) or —O($CH_2C_6H_5$);

$R^8$ is —$(CH_2)_bCOOH$;

$R^9$ is methyl, chloro, nitro, hydroxy, methoxy or —$NHR^{10}$;

$R^{10}$ is hydrogen, acetyl, $C_{1-4}$alkyl, —$SO_3H$, —$SO_2CH_3$, —$SO_2CF_3$, —$SO_2C_6H_5$, or $C_{1-4}$alkoxycarbonyl;

$R^{11}$ is phenyl or phenyl mono- or disubstituted independently with fluorine, trifluoromethoxy, $C_{1-4}$alkylthio, —$(CH_2)_cCOOH$, —$(CH_2)_cCOO(C_{1-4}$alkyl), —$(CH_2)_cSCH_3$, —$(CH_2)_cSOCH_3$, —$(CH_2)_cSO_2CH_3$, —$(CH_2)_cCONH_2$, —$SCH_2COOH$, —$CONH(SO_2CH_3)$, —$CONH(SO_2CF_3)$, —$(CH_2)_cN(C_{1-4}$alkyl)$_2$, —$(CH_2)_cNH(SO_2CF_3)$, —$(CH_2)_cN(SO_2CF_3)(C_{1-4}$alkyl), —$(CH_2)_cSO_2NHCO(C_{1-4}$alkyl), —$(CH_2)_cSO_2N(C_{1-4}$alkyl)CO($C_{1-4}$alkyl), —$(CH_2)_cCONHSO_2(C_{1-4}$alkyl), —$(CH_2)_cCON(C_{1-4}$alkyl)$SO_2(C_{1-4}$alkyl), —$(CH_2)_cOR^{12}$ —$(CH_2)_cNHR^{10}$ or phenyl monosubstituted with —$(CH_2)_c$(tetrazolyl), —$(CH_2)_c$(carboxamidotetrazolyl) or —$(CH_2)_c$(pyrrolidinyl) or $R^{11}$ is selected from pyridine and pyridinyl mono- or disubstituted independently with halogen, methyl, hydroxy, nitro, cyano, carboxy, —O($C_{1-4}$ alkyl), amino, dimethylamino, or —$NHR^{10}$;

$R^{12}$ is hydrogen, $C_{1-6}$alkyl, $C_{3-6}$cycloalkyl, —$CH_2C_6H_5$, —$CH_2COOH$, —$CH_2CONH_2$, —$CH_2CONH(C_{1-4}$alkyl), —$CH_2CON(C_{1-4}$alkyl)$_2$ or

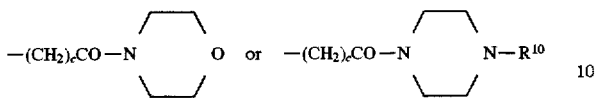

z is 1 or 2;
n is 1 or 2;
p is an integer from 1–4;
b is an integer from 0–3; and
c is 0 or 1;

together with one or more pharmaceutically acceptable carriers wherein the formulation is encased in an enteric coating or capsule.

2. A pharmaceutical composition as claimed in claim 1 wherein $R^1$ represents the group of Formula (II) wherein $R^6$ is methyl, $R^7$ is hydrogen, hydroxyl, methoxy or fluorine and n is 1 or $R^1$ represents the group $NR^4R^5$ wherein $R^4$ represents $C_{3-6}$ alkyl, cyclohexyl or phenyl, and $R^5$ represents $C_{3-6}$ alkyl or phenyl optionally substituted in the para position by hydroxy, dimethylamino, methoxy, fluorine, pyrrolidino or morpholio.

3. A pharmaceutical composition as claimed in claims 1 wherein $R^1$ represents the group $NR^4R^5$ and $R^4$ represents propyl or isopropyl and $R^5$ represents phenyl or phenyl substituted in the para position by a group selected from hydroxy, methoxy, dimethylamino, fluorine, and morpholino.

4. A pharmaceutical composition as claimed in any of claim 1 wherein $R^2$ represents a group selected from phenyl (optionally substituted by one or two groups which may be the same or different and selected from chlorine, fluorine, amino, hydroxy or carboxy,) and $NHR^{11}$ wherein $R^{11}$ is phenyl (optionally substituted by fluoro, hydroxy, amino, dimethylamino, trifluoromethylsulphonylamino, $C_{1-4}$ alkoxycarbonyl, carboxy, 1H-tetrazol-5-yl, acetylamino or $OR^{12}$ wherein $R^{12}$ represents hydrogen, methyl, benzyl, $CH_2CO_2H$, $CH_2CONH_2$, $CH_2CONHCH_3$, $CH_2CON(CH_3)_2$

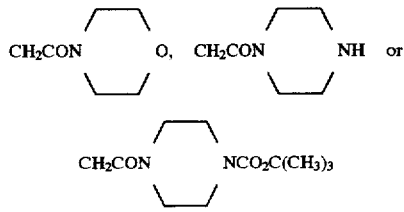

or 7-indazolyl wherein the N-1 substituted is hydrogen, or $R^2$ represents an indole group wherein the nitrogen atom is optionally substituted by the group —$CH_2CO_2H$ and the benzo ring is optionally substituted by a group selected from chlorine, methyl, methoxy, nitro, hydroxy or amino.

5. A pharmaceutical composition as claimed in claim 1 wherein $R^2$ represents an indole group which is unsubstituted on the nitrogen atom and in which the benzo ring thereof is optionally substituted by a group selected from chlorine, methyl, methoxy, nitro, hydroxy and amino.

6. A pharmaceutical composition as claimed in claim 1 wherein $R^3$ represents hydrogen, methyl, cyclohexyl,2-fluorophenyl or phenyl.

7. A pharmaceutical composition as claimed in claim 1 wherein $R^3$ represents phenyl.

8. A pharmaceutical composition as claimed in claim 1 wherein X represents hydrogen.

9. A pharmaceutical composition as claimed in claim 1 wherein $R^1$ represents $NR^4R^5$ and $R^4$ represents isopropyl and $R^5$ represents p-methoxyphenyl; $R^2$ represents an unsubstituted 2-indole group; $R^3$ represents phenyl and X represents hydrogen and enantiomers thereof.

10. A pharmaceutical composition as claimed in claim 1 in the form of an enterically coated tablet.

* * * * *